United States Patent
Lamraoui et al.

(10) Patent No.: US 11,612,354 B2
(45) Date of Patent: *Mar. 28, 2023

(54) SYSTEM AND METHOD FOR DETECTING AN ENDO-URETHRAL DEVICE FOR AN ARTIFICIAL SPHINCTER THAT IS IMPLANTABLE IN AN ANIMAL OR HUMAN BODY

(71) Applicants: UROMEMS, Grenoble (FR); ASSISTANCE PUBLIQUE—HOPITAUX DE PARIS, Paris (FR)

(72) Inventors: Hamid Lamraoui, Grenoble (FR); Pierre Mozer, Vincennes (FR)

(73) Assignee: ASSISTANCE PUBLIQUE—HOPITAUX DE PARIS, Paris (FR)

( * ) Notice: Subject to any disclaimer, the term of this patent is extended or adjusted under 35 U.S.C. 154(b) by 139 days.

This patent is subject to a terminal disclaimer.

(21) Appl. No.: 16/912,503

(22) Filed: Jun. 25, 2020

(65) Prior Publication Data

US 2020/0323487 A1    Oct. 15, 2020

Related U.S. Application Data

(63) Continuation of application No. 14/764,405, filed as application No. PCT/EP2014/051943 on Jan. 31, 2014, now Pat. No. 10,736,563.

(30) Foreign Application Priority Data

Feb. 1, 2013 (FR) ..................................... 1350880

(51) Int. Cl.
*A61F 2/00* (2006.01)
*A61B 5/11* (2006.01)
(Continued)

(52) U.S. Cl.
CPC .......... *A61B 5/4851* (2013.01); *A61B 5/1116* (2013.01); *A61B 5/205* (2013.01); *A61F 2/004* (2013.01); *A61F 2002/047* (2013.01)

(58) Field of Classification Search
CPC .. A61N 2/0004; A61N 2/0031; A61N 2/0036; A61N 2/004; A61B 5/1116; A61B 5/205; A61B 5/4851
See application file for complete search history.

(56) References Cited

U.S. PATENT DOCUMENTS 3,744,063 A    7/1973    McWhorter et al.
4,878,889 A    11/1989    Polyak
(Continued)

FOREIGN PATENT DOCUMENTS

JP    03-057448 A    3/1991
WO    01/50833 A2    7/2001
(Continued)

OTHER PUBLICATIONS

Anusionwu et al., "Indications for Revision of Artificial Urinary Sphincter and Modifiable Risk Factors for Device-Related Morbidity", Neurourology and Urodynamics, Wiley, Feb. 2012, 3 pages.
(Continued)

*Primary Examiner* — Carrie R Dorna
(74) *Attorney, Agent, or Firm* — Thomas | Horstemeyer, LLP

(57) ABSTRACT

The invention relates to a detection system of an endo-urethral device for an artificial urinary sphincter implantable in the body of a patient, said sphincter comprising an occlusive cuff (2) adapted to compress the urethra, the bladder neck or the prostate of said patient, an activation device (5) of said cuff (2) and a control unit (6) adapted to control the activation device.
Said system comprises at least one compression sensor (13) of the urethra and a posture sensor (9), and a processing unit (30) configured to determine:
(Continued)

(i) if the compression parameter of the urethra exceeds a predetermined threshold during a predetermined period, (ii) if the patient is in a recumbent position.

If the conditions (i) and (ii) are fulfilled, the processing unit sends to the activation device (5) an immediate reduction order of the compression exerted by the cuff (2).

7 Claims, 5 Drawing Sheets

(51) Int. Cl.
*A61F 2/04* (2013.01)
*A61B 5/20* (2006.01)
*A61B 5/00* (2006.01)

(56) References Cited

U.S. PATENT DOCUMENTS

| | | | |
|---|---|---|---|
| 5,478,305 A | * | 12/1995 | Craggs ............... A61F 2/004 |
| | | | 128/DIG. 25 |
| 5,509,888 A | | 4/1996 | Miller |
| 5,704,893 A | | 1/1998 | Timm |
| 6,135,945 A | | 10/2000 | Sultan |
| 6,162,238 A | | 12/2000 | Kaplan et al. |
| 7,217,237 B2 | | 5/2007 | Wassermann et al. |
| 10,383,714 B2 | | 8/2019 | Cinquin et al. |
| 2008/0177398 A1 | | 7/2008 | Gross et al. |
| 2008/0300449 A1 | | 12/2008 | Gerber et al. |
| 2009/0247817 A1 | * | 10/2009 | Forsell ............... A61M 60/268 |
| | | | 607/113 |
| 2011/0124955 A1 | | 5/2011 | Ciquin et al. |
| 2012/0157759 A1 | | 6/2012 | Wirbisky et al. |

FOREIGN PATENT DOCUMENTS

| | | |
|---|---|---|
| WO | 03/43534 A2 | 5/2003 |
| WO | 2009/027196 A1 | 3/2009 |

OTHER PUBLICATIONS

French Search Report and Written Opinion, dated Jul. 17, 2013, French Application No. 1350880.

International Preliminary Reporton Patentability received for PCT Patent Application No. PCT/EP2014/051943, dated Aug. 13, 2015, 13 pages (7 pages of English Translation and 6 pages of Original Document).

International Search Report and Written Opinion received for PCT Patent Application No. PCT/EP2014/051943, dated Feb. 28, 2014, 17 pages (8 pages of English Translation and 9 pages of Original Document).

Lamraoui et al., "Development of a Novel Artificial Urinary Sphincter: A Versatile Automated Device", IEEE/ASME Transactions on Mechatronics, vol. 15, No. 6, Dec. 2010, pp. 916-924.

Mulholland et al., "The artificial urinary sphincter and urinary catheterization: What every physician should know and do to avoid serious complications", International Urology and Nephrology, vol. 36, Jun. 2004, pp. 197-201.

Office Action received for European Patent Application No. 14702261.0, dated Sep. 12, 2018, 4 pages of Original Document Only.

* cited by examiner

SYSTEM AND METHOD FOR DETECTING AN ENDO-URETHRAL DEVICE FOR AN ARTIFICIAL SPHINCTER THAT IS IMPLANTABLE IN AN ANIMAL OR HUMAN BODY

FIELD OF THE INVENTION

The invention relates to a system for detection of an endo-urethral device for an artificial sphincter implantable in an animal or human body, as well as a detection method of the introduction of an endo-urethral device in a patient wearing such a sphincter.

BACKGROUND OF THE INVENTION

Treatment of urinary incontinence can involve implanting an artificial sphincter in a patient.

Such a sphincter typically comprises an occlusive cuff placed around the urethra (in men or women) or sometimes the bladder neck (in women) or the prostate in men with the aim of exerting direct or indirect compression on the urethra to prevent urinary leaks, an activation device of said cuff to vary compression exerted on the urethra or the bladder neck, as well as a control unit of the activation device.

Such an artificial sphincter is described in particular in [1].

Different technologies of artificial sphincters have been proposed, based in particular on different types of occlusive cuffs and associated activation mode.

According to an embodiment, the occlusive cuff is an inflatable cuff filled with fluid.

The compression device is a hydraulic device, comprising a reservoir of said fluid and an electromechanical actuator for adding or withdrawing said fluid to compress or decompress the part occluding.

Such an artificial sphincter is described for example in [2].

Another example of artificial sphincter is described in [3].

There is also a sphincter based on mechanical operation, wherein the occlusive cuff is a band surrounding the urethra or the bladder neck and connected to a strap which exerts more or less strong mechanical tension on the band by means of an electromechanical actuator [4].

When the patient must undergo an endo-urethral procedure, typically urethral catheterization, wherein, as illustrated in FIG. 1, a probe is introduced into the urethra as far as the bladder and very strong pressure is exerted on the urethra in the region surrounded by the occlusive cuff.

It is therefore recommended that practitioners release pressure exerted by the cuff prior to proceeding with insertion of the instrument or probe and throughout insertion by deactivating the artificial sphincter [5].

In fact, in the absence of such a precaution, this excessive pressure is responsible for the phenomenon of erosion of the urethra by creating a breach in its wall, causing the cuff to partially or totally be in the space of the urethra.

This erosion of the urethra involves surgical intervention to remove the cuff or even the entire artificial sphincter. Once the urethra scars over, requiring several months, a new artificial sphincter can be implanted.

Urethral erosion following an endo-urethral procedure, and quite particularly after placing a probe, is a major cause for revision of the implant.

Of revision cases connected with urethral erosion, over half are due to urethral catheterization occurring while the cuff was compressing the urethra [6].

In this respect, some clinicians estimate that the probe damages the urethra as soon as it passes through the region surrounded by the occlusive cuff; other clinicians however think that erosion occurs when excessive compression is applied beyond a certain period.

In addition, insertion of the probe can cause deterioration of the occlusive cuff and/or of the associated activation device due to the very high pressure generated.

In any case, during an endo-urethral procedure such as catheterization or introduction of a fibroscope for example it is preferable that compression of the urethra is released from insertion of the endo-urethral device and throughout the presence of the latter in the urethra.

In principle, the patient or nursing personnel can control decompression of the cuff by control means provided in the artificial sphincter.

However, there are situations wherein this prior decompression is not possible.

Such is the case for example of surgical intervention performed urgently on a patient, the nursing personnel not necessarily having knowledge of the presence of the implanted artificial sphincter.

To ensure, even in such a situation, that the endo-urethral procedure does not damage the urethra, the aim is to therefore provoke automatic decompression of the cuff during insertion of the device.

However, to prevent accidental urinary leaks, it is necessary for this decompression to be caused only when an endo-urethral device is really introduced into the urethra.

Now, there are situations where pressure exerted on the urethra is very high without a urethral probe having been introduced.

So, when the patient is seated it is possible for him to press strongly on his perineum, causing a rise in compression of the same order as that caused by the introduction of a probe.

A simple measurement of the compression of the urethra therefore fails to reliably detect an endo-urethral procedure.

BRIEF DESCRIPTION OF THE INVENTION

An aim of the invention is therefore to propose a detection system for an implantable artificial sphincter which orders the immediate decompression of the occlusive cuff as soon as introduction of a device inside the urethra is detected and which minimises the risk of incorrect detection.

Another aim of the invention is to adapt compression of the cuff as a function of the patient to prevent leaks between the endo-urethral device and the wall of the urethra in the case of patients, in particular paraplegic, who are wearers of an artificial sphincter and who must be catheterised regularly.

Preferably, the invention must also avoid any risk of damage to the activation device of the cuff under the effect of considerable stress exerted on the latter by the endo-urethral device.

According to the invention, a detection system pour an artificial urinary sphincter implantable in the body of a patient is proposed, said sphincter comprising an occlusive cuff adapted to compress the urethra, respectively the bladder neck or the prostate of said patient, an activation device of said cuff for adjusting the compression exerted by the cuff and a control unit adapted to control the activation device.

Said detection system comprises:
- at least one sensor called «compression sensor» adapted to measure a compression parameter of the urethra, respectively of the bladder neck or of the prostate, at least one sensor called «posture sensor» adapted to measure a posture parameter of the patient, and
a processing unit configured to:
receive measurement data from said sensors,
determine, from the measurement data of the compression parameter of the urethra, respectively of the bladder neck:
(i) if the compression parameter of the urethra, respectively of the bladder neck, exceeds a predetermined threshold during a predetermined period, without an order from said control unit being sent to the activation device to reduce the compression exerted by the cuff,
determine from the measurement data of the posture parameter of the patient:
(ii) if the patient is in a lying position,
if the conditions (i) and (ii) are fulfilled, send to the activation device of the artificial urinary sphincter an immediate reduction order of compression exerted by the occlusive cuff on the urethra, respectively on the bladder neck or the prostate.

«Compression parameter of the urethra» is understood to mean any measurable value representative of the compression exerted by the cuff on the urethra. This value can result from direct measuring on the urethra but can also result from indirect measuring. For example, when the occlusive cuff is a hydraulic cuff, measuring the pressure in the cuff—or even at another point of the hydraulic activation of the cuff—evaluates the compression of the urethra.

«Posture parameter» is understood to mean any measurable value representative of the posture of the patient, especially whether he is or is not in a lying position. In fact, when the patient undergoes urethral catheterization he is placed in a recumbent position. This value can result for example from an accelerometric measurement indicating the orientation of the body of the patient relative to terrestrial gravity.

«Reduction of the compression exerted by the cuff» is understood to mean either a decrease of the compression exerted until there is a non-zero value, or total release of the cuff, corresponding to zero compression.

Particularly advantageously, said at least one posture sensor and the processing unit are configured to determine if the patient is in the recumbent position (more particularly in decubitus dorsal, or else in some cases in a sloped supine position or in a gynaecological position) and to calculate the acceleration of said patient to determine if said patient is substantially immobile.

Preferably, said at least one posture sensor is selected from an accelerometer, a gyroscope and an inclinometer.

Advantageously, the compression sensor is adapted to measure an operating parameter of the activation device of the cuff and the processing unit is configured to determine, from measuring said parameter, the compression of the urethra.

According to an embodiment, the activation device of the cuff is a hydraulic device adapted for adjusting pressure of fluid in the occlusive cuff.

In this case, said at least one compression sensor is advantageously a pressure sensor arranged to measure the pressure of fluid in said hydraulic device.

According to another embodiment, the activation device of the cuff is a device adapted for adjusting mechanical tension of the occlusive cuff.

In this case, the compression sensor is preferably a mechanical strain sensor.

According to a particularly advantageous embodiment, the detection system also comprises an element for reducing mechanical stresses undergone by the activation device.

According to a particular embodiment of the invention, in the case of a hydraulic activation device, said element comprises an expansion chamber arranged in the hydraulic device for transferring some of the volume of fluid in said expansion chamber to reduce to a value defined the pressure in the hydraulic device.

According to an advantageous embodiment, the processing unit is integrated into the control unit of the artificial urinary sphincter.

Preferably, the processing unit or the control unit is configured to send an audio signal prior to reduction of the compression exerted by the cuff.

Also, the processing unit advantageously comprises a memory on which is recorded a computer program, said program comprising instructions fro performing the following steps:
(S101) reading a signal of a compression parameter of the urethra, respectively of the bladder neck,
(S102) comparison of said signal with a predetermined threshold,
(S105) if the compression parameter of the urethra, respectively of the bladder neck or of the prostate, exceeds said predetermined threshold during a predetermined period, reading a signal of a posture parameter of the patient, if not return to step S101,
(S107) comparison of a parameter of said signal with a predetermined upper limit, and determination of an immobile position of the patient if said parameter is less than said upper limit,
(S109) determination, from said signal, of the position of the patient in decubitus dorsal,
(S110) repetition of the preceding steps during a predetermined number of iterations,
(S114) sending to the activation device of the artificial urinary sphincter an immediate reduction order of the compression exerted by the occlusive cuff on the urethra, respectively on the bladder neck.

Optionally, said at least one posture sensor and the processing unit are configured to determine if the patient is in a seated position and to determine if the torso of said patient is substantially immobile.

In this case, the condition (ii) for sending the immediate reduction order of the compression exerted by the cuff is when the patient is seated.

This usefully allows taking the particular case of paraplegic patients into account.

Finally, advantageously the processing unit is configured, if said compression parameter of the urethra exceeds a predetermined safety threshold greater than the threshold relative to which said parameter is compared in the evaluation of the condition (i), to send an immediate reduction order of the compression exerted by the cuff, irrespective the status of the condition (ii).

Another object relates to an artificial urinary sphincter comprising a detection system such as described hereinabove.

Said sphincter comprises:
an occlusive cuff adapted to compress the urethra, respectively the bladder neck or the prostate of a patient in whom it is intended to be implanted,
an activation device of said cuff for adjusting the compression exerted by the cuff,
a control unit adapted to control the activation device, and a detection system such as described hereinabove, which communicates with the activation device.

The invention also relates to a detection method of the introduction of an endo-urethral device in a patient wearing an artificial urinary sphincter, said sphincter comprising an occlusive cuff adapted to compress the urethra, respectively the bladder neck or the prostate of said patient, an activation device of said cuff for adjusting the compression exerted by the cuff and a control unit adapted to control the activation device, wherein:

at least one compression parameter of the urethra, respectively of the bladder neck or of the prostate, is measured, a posture parameter of the patient is measured, from the measurement data of the compression parameter of the urethra, respectively of the bladder neck it is determined:

(i) if the compression parameter of the urethra, respectively of the bladder neck, exceeds a predetermined threshold during a predetermined period without an order of said control unit being sent to the activation device to reduce the compression exerted by the cuff, from the measurement data of the posture parameter of the patient it is determined:

(ii) if the patient is in a lying position, if the conditions (i) and (ii) are fulfilled, the introduction of an endo-urethral device is detected.

According to a particularly advantageous embodiment of said method, if the mechanical stresses undergone by the activation device are greater than a threshold de stresses determine, a stress-reduction element is activated so as to diminish said stresses in the activation device and maintain compression exerted by the cuff above the detection threshold.

BRIEF DESCRIPTION OF DRAWINGS

Other characteristics and advantages of the invention will emerge from the following detailed description, in reference to the attached drawings, wherein.

DETAILED DESCRIPTION OF EMBODIMENTS OF THE INVENTION

Artificial Urinary Sphincter

In general, an artificial sphincter comprises an occlusive cuff designed to be implanted around the urethra, or optionally the bladder neck in women or the prostate in men, so as to compress the urethra to avoid urinary leaks, especially in the event where the patient suffers from effort incontinence.

The artificial sphincter also comprises an activation device for adjusting the compression exerted by the cuff.

In the oldest known artificial sphincters, this activation device was controlled manually by the patient, for example by pressure exerted on a pump device arranged under the skin.

Currently, more refined systems are under development to spare the patient manual pressure on the pump to control the cuff.

The artificial sphincter comprises a control unit, also implanted in the body of the patient, adapted to control the activation device of the cuff.

There are currently different artificial sphincters, utilising different cuff technologies (hydraulic, mechanical, etc.) and different associated actuation technologies (piezo-electric actuator, cables, straps, memory shape devices, etc.).

The man skilled in the art knows these different artificial sphincters.

Reference could be made for example to the following documents [1] to [4] cited above or to documents [7] and [8].

The invention is not limited to any one particular sphincter technology.

In the following text, by way of illustration the case of introduction of a urethral probe is considered, but the invention applies to detection of the introduction of any endo-urethral device, irrespective of the function of this device. «Endo-urethral device» is understood to mean any device designed to be inserted into the urethra of a patient with a view to access the urethra, the bladder neck or the bladder, irrespective of the finality of this device. Examples of endo-urethral devices, apart from probes, are dilators, fibroscopes whether supple or rigid.

Figure 1:
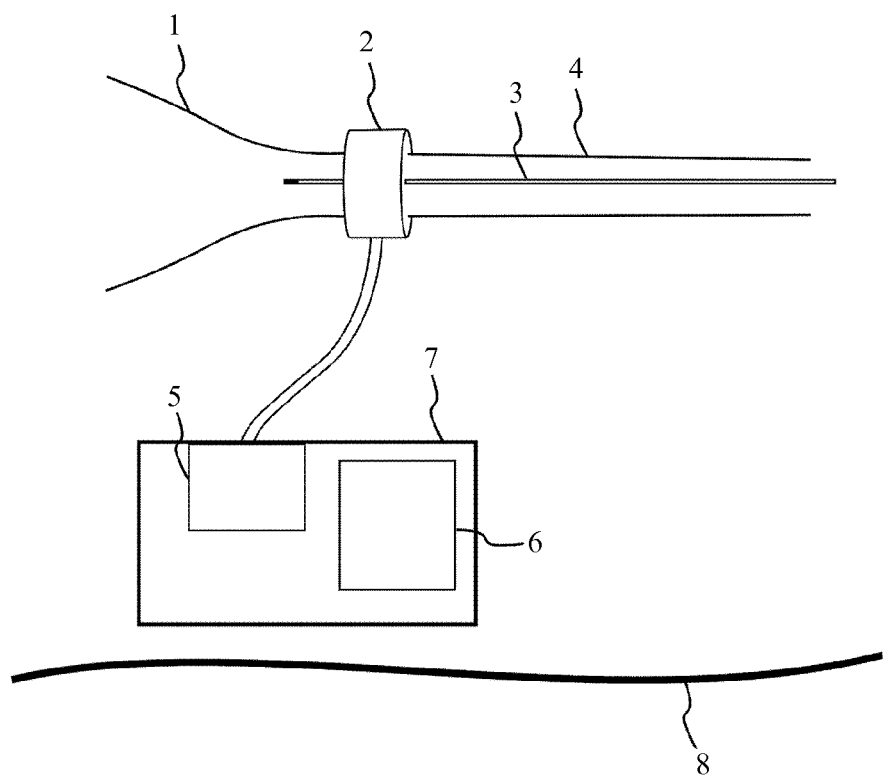
FIG. 1 is a schematic view of the introduction of a urethral probe in a patient fitted with an artificial urinary sphincter, FIG. 2 schematically illustrates measuring a posture parameter of the patient.

FIG. 1 schematically illustrates the introduction of a urethral probe into a patient fitted with an artificial urinary sphincter.

The artificial sphincter comprises an occlusive cuff 2 surrounding the part 1 to be occluded (specifically according to case urethra, bladder neck or prostate) of the patient, and a control box 7 also implanted in the body of the patient (reference 8 designates the skin of the patient).

The box is made of biocompatible material and is designed to protect the components of the sphincter other than the cuff.

Said box comprises the activation device 5 of the cuff 1, connected to the cuff by a link whereof the nature depends of the activation mode of the cuff.

For example, within the scope of a hydraulic cuff, the activation device comprises a reservoir and the link is tubing 17 filled with fluid which can be transferred bidirectionally from the cuff to the reservoir according to whether the aim is to increase or decrease the compression exerted. In terms of a band surrounding the urethra, the activation device can be an electromechanical system coupled to a cable 20 for exerting compression on the urethra.

The box 7 also comprises the control unit 6, connected to the activation device by any appropriate means.

During urethral catheterization, an endo-urethral device 3 is introduced into the urethra, including the part surrounded by the cuff.

The detection system described hereinbelow relaxes (either fully or partially) the compression exerted by the occlusive cuff as soon as introduction of the endo-urethral device is detected.

Detection System

For this purpose, the detection system (not illustrated in FIG. 1) comprises the following components.

First, the system comprises at least one sensor called «compression sensor» adapted to measure a compression parameter of the urethra or of the bladder neck.

For the sake of concision mention will be made throughout the following text of compression of the urethra, but it is understood that this also covers, where appropriate, compression of the bladder neck in women or the prostate in men.

Said sensor can measure compression of the urethra directly, that is, by being placed on the wall of the urethra.

Alternatively, said sensor can measure compression of the urethra indirectly, that is, by measuring a compression value associated with one of the components of the artificial sphincter.

So, for example, in the event where the artificial sphincter comprises a hydraulic cuff activated by a reservoir, the compression sensor can be a pressure sensor arranged against a wall of said reservoir to measure the pressure in the hydraulic circuit.

Calibration establishes the relation between the pressure of the hydraulic circuit measured by the sensor and the compression exerted on the urethra.

Mention will be made throughout the following text therefore of «compression parameter of the urethra» to designate the result of the measurement given by the sensor, representative of the compression of the urethra.

Introduction of a urethral probe is translated by measuring, by said sensor, of a high value of the compression exerted on the urethra.

Therefore a threshold beyond which compression is considered as likely to be due to the introduction of a urethral probe is defined.

This threshold is determined so that neither the compressed part nor the occlusive cuff can be damaged.

Compression is not necessarily measured continuously.

In fact, for reasons of economy of energy consumed by the compression sensor, the latter can be activated and deactivated periodically.

The frequency measurement of compression results advantageously from a compromise between a high frequency ensuring reactivity of the detection system and a low frequency minimising energy consumed.

On the other hand, the detection system also comprises at least one sensor called a «posture sensor» adapted to measure a posture parameter of the patient.

«Posture» is understood to mean the activity of the patient and/or the inclination of the patient.

Examples of posture sensors usually employed in implantable systems are accelerometers, gyroscopes and inclinometers, but the invention can be implemented by means of any other adequate sensor.

According to an embodiment, the posture sensor is an accelerometer having three axes implanted in the body of the patient.

Figure 2:
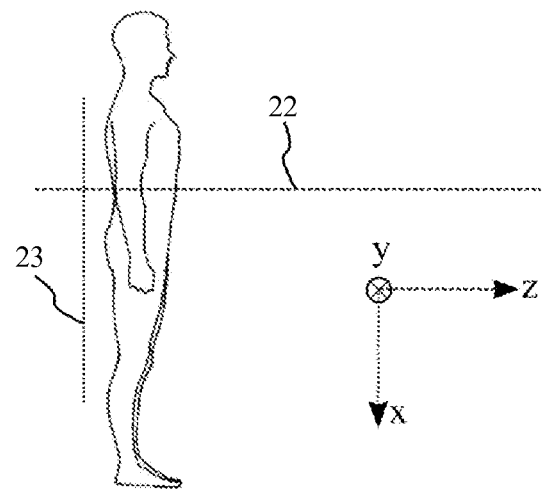

In this way, the posture parameters of the patient provided by such an accelerometer are:
- on the one hand, the activity of the patient, based for example on the accelerometric standard $|a|$, given by the formula $\sqrt{a_x^2 + a_y^2 + a_z^2}$ where $a_x$, $a_y$ and $a_z$ are the acceleration values measured for each of the axes x, y, z of the accelerometer (cf. FIG. 2),
- on the other hand, the inclination of the patient.

Determining the inclination of the patient can be based on measuring gravity by the three axes of the accelerometer.

For example, according to the axis x, an angle $\alpha = \arcsin(a_{xpb})$ is determined where $\alpha$ is the measured angle and $a_{xpb}$ is the acceleration measured by the accelerometer and filtered by a low-pass filter for recovering only the quasi-static component of the signal, corresponding to the component of gravity.

From measurement of the angle according to the vertical axis 23 of the patient and measurement of the angle according to the axis antero-posterior 22 of the patient (cf. FIG. 2), it is possible to identify a posture representative of urethral catheterization, specifically the posture decubitus dorsal, more particularly, when the patient has at least his torso prone on his back.

It is not necessary in this respect to determine a precise inclination of the body of the patient; it suffices to identify if the latter is lying down, on his back or on his stomach.

Advantageously, said sensor can be in the box 7.

In this way, taking into account the posture of the patient while a high compression value is exerted on the urethra prevents accidental decompression of the cuff.

In fact, taking into account this high value does not determine with certainty that a urethral probe is introduced.

It is not to be discounted, for example, that the patient is in a posture or is exerting activity engendering strong compression of the urethra, without any urethral probe being introduced.

In this way, when the patient is seated and is leaning strongly on his perineum, the occlusive cuff, located in the perineal region, undergoes significant compression, embodied by substantial pressure in the hydraulic circuit, and strong compression of the urethra can be measured.

The posture sensor avoids false detection of the introduction of a urethral probe.

In fact, urethral catheterization can be associated with some specific postures of the patient, specifically:
- the fact that the patient is lying down,
- where appropriate, the fact that the patient is substantially immobile.

Consequently, the combination of the detection:
- of high compression exerted on the urethra for a determined period, sufficiently long to be significant, and
- of a posture of the patient corresponding to a urethral catheterization situation, determines with a degree of sufficient certainty that urethral catheterization is being practiced on the patient.

As for the compression sensor, the posture sensor is not necessarily activated continuously so as to minimise its power usage.

The detection system advantageously comprises a clock for measuring the period during which a pressure value greater than a determined threshold is measured.

For example, said threshold of duration can be fixed at a few seconds.

The detection system further comprises a processing unit configured to receive, via a wire link or a wireless link, measurement data from the compression and posture sensors and to determine:
- from the measurement data of the compression parameter of the urethra if said parameter exceeds a predetermined threshold during a predetermined period without an order of the control unit being sent to the activation device to reduce the compression exerted by the cuff (condition (i)),
- from the measurement data of the posture parameter of the patient if the patient is in a lying position and substantially immobile (condition (ii)).

If the conditions (i) and (ii) are fulfilled, the processing unit sends the activation device an immediate reduction order of the compression exerted by the occlusive cuff on the urethra.

Optionally, the processing unit or the control unit is configured to send an audio signal prior to reduction of the compression exerted by the cuff.

Said processing unit can typically comprise a microcontroller.

The clock mentioned earlier can be included in said microcontroller.

On the other hand, the microcontroller can optionally comprise other clocks, especially for managing activation and deactivation of the compression and posture sensors to limit the power usage of the latter.

Figure 3:
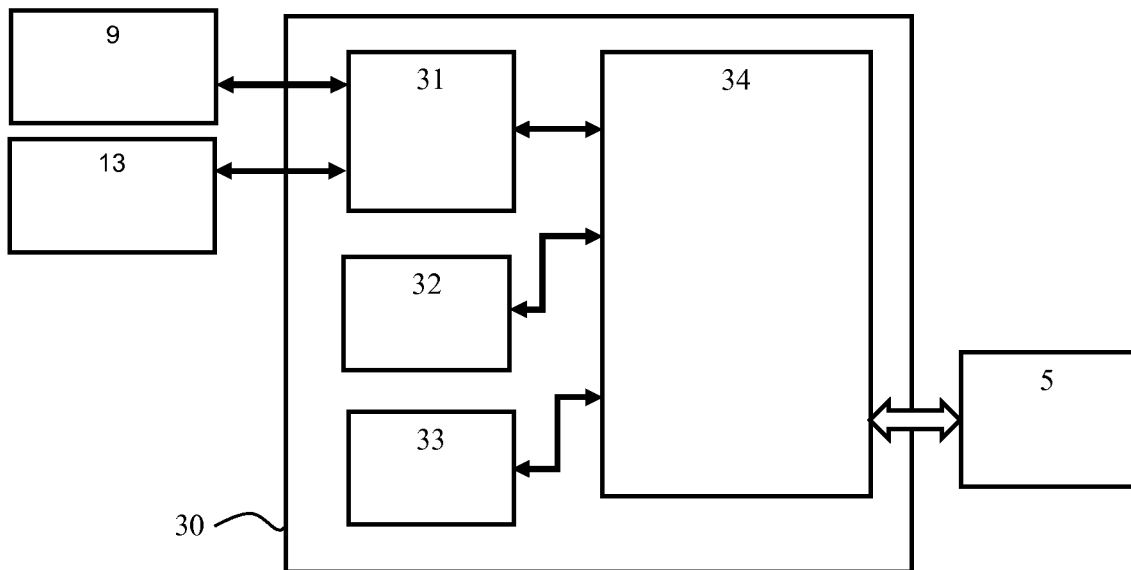
FIG. 3 illustrates the general architecture of the detection system according to an embodiment of the invention, FIGS. 4 to 6 schematically illustrate different configurations of the detection system and the artificial urinary sphincter.

FIG. 3 illustrates an embodiment of the general architecture of the detection system.

The processing unit 30 communicates with the compression sensor 13 and the posture sensor 9 by means of an interface 31.

The communication is indicated by arrows and can be made via a wire link or a wireless link, according to known protocols.

The processing unit 30 also comprises a memory 32 wherein the thresholds and parameters mentioned above are recorded.

The processing unit also comprises one or more clocks 33.

A microcontroller 34 is connected to the interface 31, the memory 32 and the clock 33.

The microcontroller 34 is adapted to implement an algorithm to be described in detail below and to communicate with the activation device 5 of the cuff so as to send it a decompression order if the conditions of urethral catheterization are combined.

Figure 4:
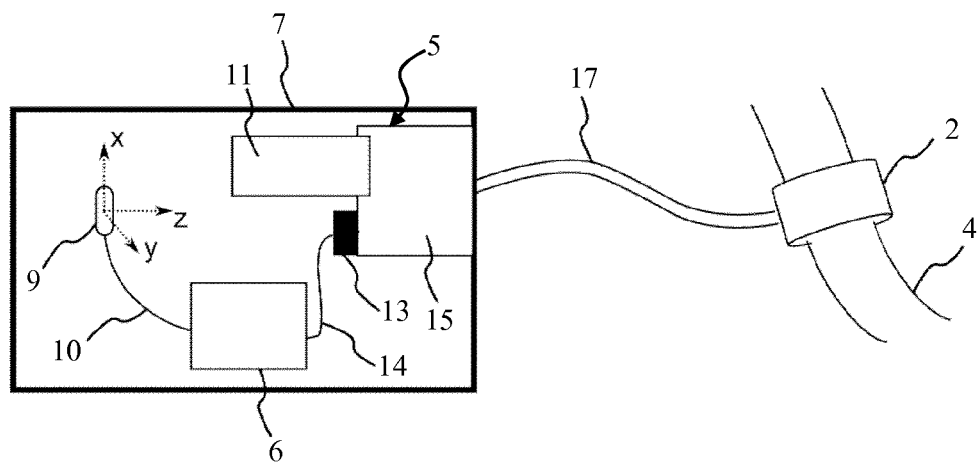
Figure 5:
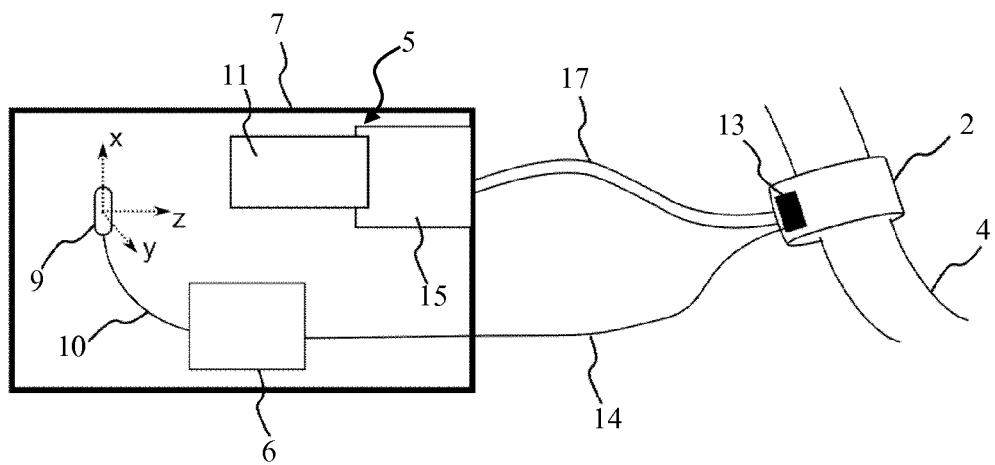
Figure 6:
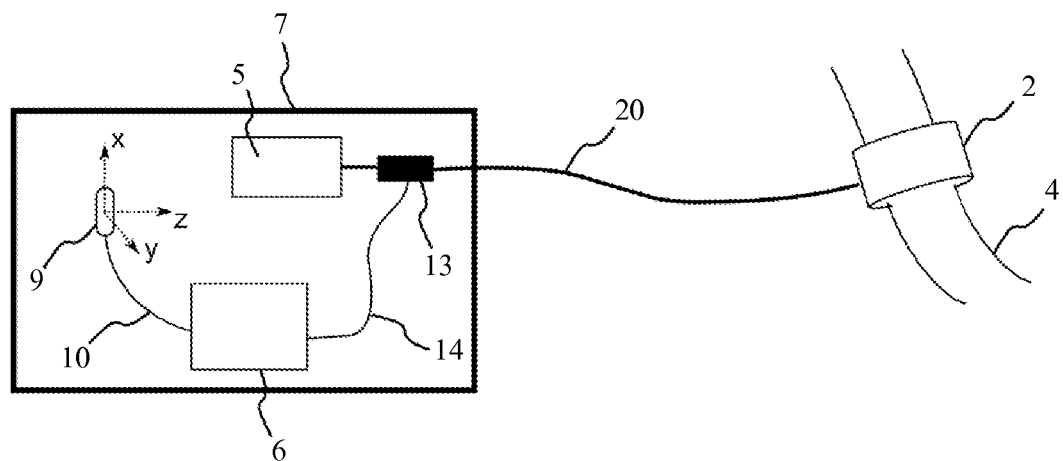

FIGS. 4 to 6 illustrate different non-limiting embodiments of the detection system.

In these three embodiments, the processing unit is integrated into the control unit and is therefore not illustrated as such.

However it is understood that the processing unit could be installed at another placement, in the box 7 or outside the latter without as such departing from the scope of the present invention.

Case of a Sphincter Comprising a Hydraulic Activation Device of the Occlusive Cuff FIG. 4 illustrates an embodiment of the detection system for a sphincter wherein the cuff 2 is a hydraulic cuff and the activation device 5 of the cuff comprises a reservoir 15 of variable volume in fluid communication with the cuff via tubing 17, as well as an actuation mechanism 11 for imposing displacement of the fluid from the reservoir 15 to the cuff 2 or inversely from the cuff 2 to the reservoir 15.

For example, the actuation mechanism 11 can be an actuator adapted to vary the volume of the reservoir 15 by generating relative displacement of two opposite walls.

The compression sensor 13 is a pressure sensor arranged against a membrane (not shown) arranged in a wall 15 of the reservoir for measuring the pressure in the hydraulic circuit.

It is connected via a link 14, wired or wireless, to the processing unit integrated into the control unit 6.

The posture sensor 9 is an accelerometer having three axes x, y, z, which is connected via a link 10, wired or wireless, to the processing unit integrated into the control unit 6.

FIG. 5 illustrates a variant of the embodiment of FIG. 4, wherein the pressure sensor is placed in contact with the cuff 2 to measure the pressure in said cuff.

Case of a Sphincter Comprising a Device for Activation by Cable of the Occlusive Cuff FIG. 6 illustrates an embodiment of a detection system for a sphincter wherein, contrary to the examples described in FIGS. 4 and 5, the activation device of the cuff is not based on hydraulic but mechanical operation.

Said device is adapted for adjusting mechanical tension of the occlusive cuff.

The link between the cuff 2 and the activation device 5 can be ensured by a cable 20.

In this configuration, the compression sensor 13 is a sensor capable of measuring a mechanical force, for example the mechanical tension of the cable 20.

The sensor is shown here inside the box 7, but it could alternatively be placed outside the latter.

As in the preceding example, the posture sensor 9 is an accelerometer arranged in the box 7.

The sensors 9 and 13 are connected by links 10 and 14 to the processing unit which is integrated into the control unit 6.

Detection Method

Figure 7:
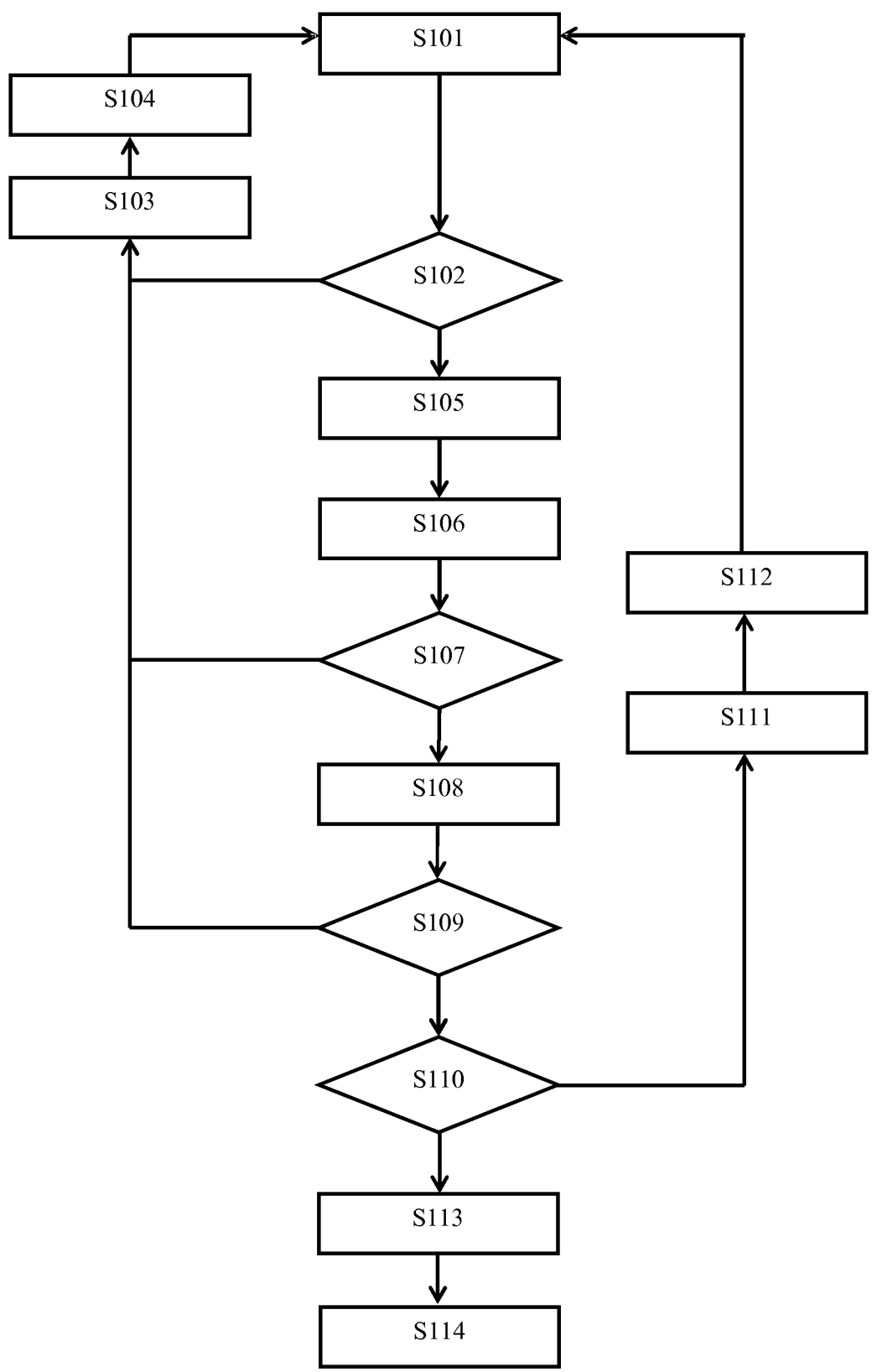
FIG. 7 is a logigram presenting the steps of the detection method for introduction of an endo-urethral device into a patient wearing an artificial urinary sphincter, FIG. 8 schematically illustrates a configuration of an artificial urinary sphincter comprising a reduction element of mechanical stresses undergone by the activation device.

The steps of the detection method for introduction of an endo-urethral device into a patient wearing the artificial urinary sphincter are illustrated on the logigram of FIG. 7. Said sphincter has been implanted in the patient previously and the invention does not cover this prior implantation step.

This algorithm is recorded in the memory of the detection system and executed by the processing unit.

Naturally, this is just one example and steps could be added or implemented differently without departing from the scope of the invention.

Step S101: activation of the compression sensor; reading a signal of a compression parameter of the urethra coming from the compression sensor; deactivation of the sensor once measurement is taken (this sequence can be repeated several times during this step)

Step S102: comparison of the compression signal with a predetermined threshold,

Step S105: if the compression parameter of the urethra exceeds said predetermined threshold during a predetermined period, activation of the posture sensor, reading a signal of a posture parameter of the patient (typically, one or more acceleration measurements according to the three axes of the accelerometer (components DC and AC); deactivation of the sensor once the measurement is taken;

if not, return to step S101 by resetting a counter to 0 (step S103) and by expecting a predetermined period (step S104) before taking a new measurement; this can last from a few milliseconds to a few seconds, Step S106: calculation of the accelerometric standard from measurements according to the three axes of the accelerometer, using high-pass filtering to recover only the component AC of the signal, translating activity of the patient, Step S107: comparison of a parameter of said posture signal (for example, the accelerometric standard calculated earlier) with a predetermined upper limit, and the determination of an immobile position of the patient if said parameter is less than said upper limit, Step S108: measuring of the angle of inclination of the patient according to the vertical axis to ensure that he is lying down (in fact, measuring according to this axis gives quasi-static acceleration around 0 g, making measuring of an angle more precise around this value when the patient is lying down); measurement of quasi-static acceleration according to the antero-posterior axis of the patient for calculating the angle of inclination according to this axis to deduce whether the patient is on his back or not, Step S109: determination, from said signal, of the position of the patient in decubitus dorsal; for this purpose, each measured angle of inclination is compared to two limits, each angle having to be between these two limits, Step S110: comparison of the counter with a predetermined number of iterations; if the counter i is less than this determined number, repetition of the preceding steps from step S101 during a predetermined number of iterations; this index i ensures during a predetermined period that the patient is effectively in the method of undergoing urethral catheterization to prevent a false alarm and untimely decompression of the cuff;

Step S111: waiting for a predetermined period (this wait, combined with the number of iterations measured in step S110 being a condition for decision to send a decompression order to the cuff)

Step S112: incrementation of 1 of the number of iterations,

Step S113: reinitialisation to 0 of the counter of iterations,

Step S114: sending to the activation device of the artificial urinary sphincter of an immediate reduction order of the compression exerted by the occlusive cuff on the urethra.

Compression of the occlusive cuff after catheterization can be done either automatically after a predetermined time or manually by the patient or nursing personnel for example from an external remote communicating with the implant.

Verification by progressive recompression of the cuff and measuring of the compression pressure ensures that the probe is still inserted or has been withdrawn.

Particular Case of a Paraplegic Patient

Advantageously, measuring the posture parameter of the patient can be used for some patients, especially paraplegic patients, who are obliged to carry out urethral catheterizations themselves in a seated position.

For these patients, it is therefore necessary to consider the postural parameter in detection of the urethral catheterization in different ways.

As explained above, if the patient is in bed and pressure in the cuff increases, it will be fully opened automatically.

If the patient is seated and a rise in pressure is detected at the level of the cuff, it is the patient catheterising himself voluntarily.

In this case, the cuff can be opened not fully but just enough to let the probe pass through and avoid urinary leaks between the urethra and the probe.

This adjustment in compression can in fact prevent the appearance of leaks in the seated patient during catheterization.

Safety Systems

In the event where pressure in the hydraulic circuit or the mechanical system becomes very high and close to the limits defined in the technical recommendations concerning the pressure resistance of the different elements of the hydraulic circuit, respectively of the mechanical system, the processing unit can automatically send a decompression order of the cuff, without verifying the posture of the patient.

In this case, the safety threshold is greater than the detection threshold relative to which the compression parameter is evaluated in condition (i).

According to a particularly advantageous embodiment of the invention, the activation device of the cuff comprises an element for reducing mechanical stresses caused by excessive compression of the urethra, allowing protecting the activation device from the risk of deterioration during the period of detection of the introduction of a urethral probe.

As explained previously, the detection method comprises a wait period having a predetermined duration during which the measured compression must be greater than the pre-defined detection threshold so that introduction of a probe is identified. This wait period, relatively short, prevents false detection linked to untimely compression peaks of the urethra under detection conditions.

During this short period, the mechanical stresses undergone by the activation device resulting from substantial compression of the urethra can become quite significant, and this could cause deterioration of one or more parts of the activation device. In the case of a hydraulic activation system, the pump, the tubing, the cuff, the pressure sensor and/or the connectors can be affected by this degradation. In the case of a mechanical activation system, the cuff, the cable and/or the sensor of mechanical tension of the cable can be affected by these excessive stresses.

To prevent deterioration of the activation device, the stress-reduction element is designed so as, when mechanical stresses (pressure in the fluid circuit, mechanical tension of the cable) exceed a determined stress threshold, to absorb some of said stresses so as to reduce stresses undergone by the activation device.

The stress-reduction element is dimensioned to lower stresses to a level where they are too weak to risk damaging the activation device and are sufficiently high so as not to fully relax the compression exerted by the cuff. More precisely, to the extent where the introduction of a urethral probe is detected by comparison of compression with a predetermined threshold, compression exerted by the cuff after reduction of stresses must remain greater than said detection threshold.

As a function of the planned mode of stress reduction and the structure of the activation device, the expert can design an element fulfilling these conditions.

According to an embodiment, in the case of a hydraulic system, the stress-reduction element comprises an expansion chamber arranged in the hydraulic circuit and being triggered mechanically when the pressure in the fluid circuit exceeds a defined threshold. The effect of this is to transfer some of the fluid from the hydraulic circuit to the expansion chamber to reduce pressure in the latter.

Alternatively, the stress-reduction element can comprise a piston coupled to a spring system having sufficiently high stiffness to remain substantially fixed when the pressure in the hydraulic circuit corresponds to the normal operating pressure of the artificial sphincter (that is, typically under 200 cm $H_2O$) and mobile under the effect of higher pressure.

The aim of the stress-reduction element is not to sufficiently reduce pressure in the occlusive cuff to allow passage of a probe into the urethra at the level of the cuff, but to protect the hydraulic circuit when high stresses are applied to the latter, especially in the early stages of inserting an endo-urethral device. This element is made so as to have minimal effect during normal operation of the artificial sphincter.

Figure 8:
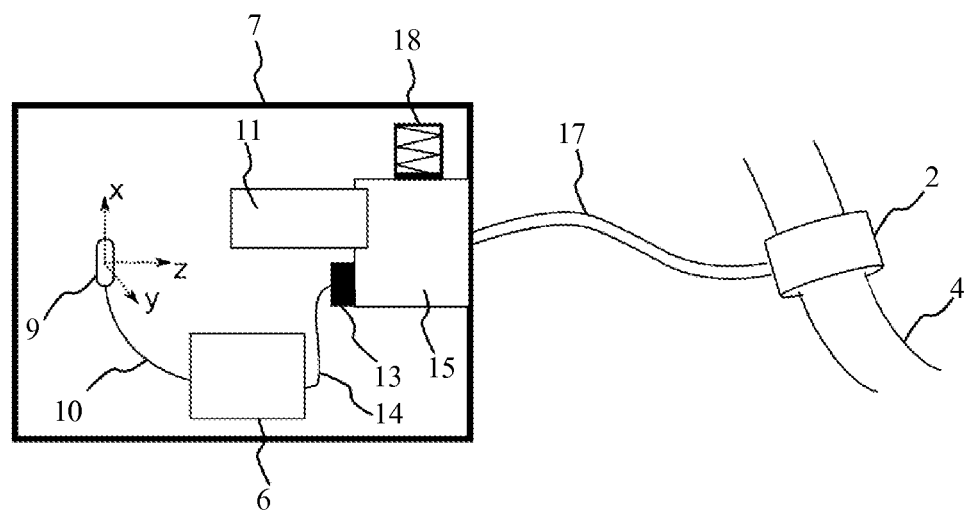

FIG. 8 illustrates a sketch of a detection system for an artificial sphincter wherein the activation device of the cuff is hydraulic. The elements fulfilling the same function as those shown in FIGS. 4 and 5 are designated by the same reference numerals and are not described further.

The stress-reduction element is designated by 18. In this figure, it is shown arranged on the reservoir 15 but it could be arranged in any other placement of the hydraulic circuit or the occlusive cuff.

The stress-reduction element can have different embodiments; for example and non-limiting:

a valve coupled to a spring or specific material in an expansion chamber;

a component of the hydraulic circuit made of flexible material having the properties of deforming from a certain pressure threshold;

a membrane deformable beyond a certain pressure threshold or as a function of the pressure applied;

the reservoir 15 designed so as to be deformable beyond a certain pressure threshold or as a function of the pressure applied;

the activation mechanism 11 designed so as to be deformable beyond a certain pressure threshold or as a function of the pressure applied.

By way of example, the stress-reduction element can operate as follows in conjunction with detection of the introduction of a urethral probe:

When a probe is introduced to the urethra, the pressure in the hydraulic circuit is such that the stress-reduction element is triggered, resulting in lowering of the pressure in the hydraulic circuit until a value greater than the detection threshold but lower than the maximal stress supported by the activation device is achieved.

It is verified that the pressure in the hydraulic circuit is greater than the detection threshold during a determined period.

From the measurement data of the posture parameter of the patient it is determined if the patient is in a recumbent position and immobile, where appropriate.

If the pressure and posture conditions are fulfilled, the introduction of an endo-urethral device is detected.

According to another embodiment, the stress-reduction element can also be applied at an artificial sphincter based on a mechanical activation system. In this case, said element can especially comprise a mechanism placed on the cable (for example, a spring system of considerable stiffness) used to absorb excessive forces during the initial instants of passage of an endo-urethral probe, prior to detection and decompression of the occlusive device.

Finally, it is understood that the examples given here are only particular illustrations and are in no way limiting as to the fields of application of the invention.

REFERENCES

[1] WO 2009/027196
[2] Development of a Novel Artificial Urinary Sphincter, H. Lamraoui et al, IEEE/ASME Transactions on Mechatronics, Vol. 15, No. 6, December 2010
[3] U.S. Pat. No. 6,162,238
[4] U.S. Pat. No. 5,704,893
[5] The artificial urinary sphincter and urinary catheterization: What every physician should know and do to avoid serious complications, T. L. Mulholland et al, International Urology and Nephrology 36: 197-201, 2004
[6] Indications for Revision of Artificial Urinary Sphincter and Modifiable Risk Factors for Device-Related Morbidity, I. I. Anusionwu et al, Neurourology and Urodynamics, Wiley, 2012
[7] U.S. Pat. No. 5,509,888
[8] U.S. Pat. No. 6,135,945

The invention claimed is:

1. An artificial urinary sphincter implantable in a body of a patient, comprising
an occlusive cuff configured to compress a selected one of a urethra, a bladder neck and a prostate of the patient,
an activation device coupled to the cuff for adjusting a compression amount exerted by the cuff, the activation device comprising
a hydraulic circuit including a reservoir and a tubing fluidly coupling the occlusive cuff and the reservoir, and
an actuator configured to transfer fluid between the reservoir and the occlusive cuff,
at least one compression sensor configured to measure a compression parameter of selected one of the urethra, the bladder neck and the prostate,
a processing unit comprising a microcontroller, a clock and a memory, configured to:
receive measurement data from the at least one compression sensor,
based on the measurement data, determine that an endo-urethral device is being introduced in the patient's body, and
selectively send to the activation device an order to reduce the compression amount exerted by the occlusive cuff on the selected one of the urethra, the bladder neck and the prostate, and
an expansion chamber selectively connected to the hydraulic circuit, a fluidic connection between the expansion chamber and the hydraulic circuit being configured to be triggered mechanically by a fluid pressure in the activation device exceeding a defined threshold to allow transferring some of the fluid from the hydraulic circuit to said expansion chamber to reduce the fluid pressure in the activation device to a defined value.

2. The artificial urinary sphincter of claim 1, further comprising at least one posture sensor, wherein the processing unit is configured to determine, based on measurement data from the posture sensor, if the patient is in a decubitus dorsal position and if said patient is substantially immobile.

3. The artificial urinary sphincter of claim 2, wherein the at least one posture sensor is selected from an accelerometer, a gyroscope and an inclinometer.

4. The artificial urinary sphincter of claim 1, wherein the at least one compression sensor is adapted to measure an operating parameter of the activation device and the processing unit is configured to determine, from the measurement of said parameter, a compression of the urethra.

5. The artificial urinary sphincter of claim 1, wherein the at least one compression sensor is a pressure sensor arranged to measure a pressure of fluid in the activation device.

6. The artificial urinary sphincter of claim 1, wherein the processing unit is integrated into a control unit of the artificial urinary sphincter.

7. The artificial urinary sphincter of claim 6, wherein the processing unit or the control unit is configured to send an audio signal prior to reduction of the compression exerted by the cuff.

* * * * *